US011020016B2

(12) United States Patent
Wallace et al.

(10) Patent No.: US 11,020,016 B2
(45) Date of Patent: Jun. 1, 2021

(54) SYSTEM AND METHOD FOR DISPLAYING ANATOMY AND DEVICES ON A MOVABLE DISPLAY

(71) Applicant: Auris Surgical Robotics, Inc., San Carlos, CA (US)

(72) Inventors: Daniel Wallace, Santa Cruz, CA (US); Gregory Stahler, San Jose, CA (US); Aaron Grogan, Scotts Valley, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 14/286,793

(22) Filed: May 23, 2014

(65) Prior Publication Data

US 2014/0357984 A1    Dec. 4, 2014

Related U.S. Application Data

(60) Provisional application No. 61/829,078, filed on May 30, 2013.

(51) Int. Cl.
*A61B 34/10*    (2016.01)
*A61B 34/20*    (2016.01)
(Continued)

(52) U.S. Cl.
CPC ............ *A61B 5/062* (2013.01); *A61B 5/7425* (2013.01); *A61B 90/37* (2016.02); *A61B 5/055* (2013.01);
(Continued)

(58) Field of Classification Search
CPC .... A61B 6/00; A61B 6/12; A61B 6/40; A61B 6/42; A61B 6/46; A61B 6/461;
(Continued)

(56) References Cited

U.S. PATENT DOCUMENTS

| 4,745,908 A | 5/1988 | Wardle |
| 4,771,262 A | 9/1988 | Reuss |

(Continued)

FOREIGN PATENT DOCUMENTS

| CN | 101147676 | 3/2008 |
| CN | 101222882 | 7/2008 |

(Continued)

OTHER PUBLICATIONS

Racadio et al., "Live 3D guidance in the interventional radiology suite," Dec. 2007, AJR, 189:W357-W364.*

(Continued)

*Primary Examiner* — Patricia J Park
(74) *Attorney, Agent, or Firm* — Morgan, Lewis & Bockius LLP

(57) ABSTRACT

An image display system is provided comprised of a virtual window system that creates a visual coherency between the patient's anatomical images and the actual patient by aligning the image on the display to the patient and then presenting the image to the user in a way that feels as if the user is looking directly into the patient through the display. The image shown within the image display system is dependent upon the position of the image display apparatus and the position of the user so that the display orientation of the image may be biased slightly toward the user to improve ergonomics and usability.

35 Claims, 4 Drawing Sheets

(51) Int. Cl.
  *A61B 34/30* (2016.01)
  *A61B 5/06* (2006.01)
  *A61B 5/00* (2006.01)
  *A61B 90/00* (2016.01)
  *A61B 6/00* (2006.01)
  *A61B 8/08* (2006.01)
  *A61B 5/055* (2006.01)

(52) U.S. Cl.
  CPC ............ *A61B 5/7445* (2013.01); *A61B 6/487* (2013.01); *A61B 8/0833* (2013.01); *A61B 2034/2051* (2016.02)

(58) Field of Classification Search
  CPC ......... A61B 6/462; A61B 6/463; A61B 6/465; A61B 6/466; A61B 6/467; A61B 6/468; A61B 6/469; A61B 6/485; A61B 6/486; A61B 6/487; A61B 6/488; A61B 6/5288; A61B 6/547; A61B 6/584; A61B 6/587; A61B 6/588; A61B 6/589; A61B 8/0841; A61B 8/085; A61B 8/46; A61B 8/461; A61B 8/462; A61B 8/463; A61B 8/466; A61B 8/467; A61B 8/468; A61B 8/52; A61B 8/5207; A61B 8/5238; A61B 8/5253; A61B 8/5261; A61B 8/5284; A61B 19/20; A61B 19/50; A61B 19/52; A61B 19/5212; A61B 19/5225; A61B 19/5244; A61B 2034/107
  USPC ....... 600/415, 420, 424, 425, 426, 429, 431, 600/443
  See application file for complete search history.

(56) References Cited

U.S. PATENT DOCUMENTS

| | | | |
|---|---|---|---|
| 4,896,554 A | | 1/1990 | Culver |
| 5,008,528 A | | 4/1991 | Duchon |
| 5,134,390 A | | 7/1992 | Kishimoto et al. |
| 5,176,310 A | | 1/1993 | Akiyama et al. |
| 5,273,025 A | | 12/1993 | Sakiyam et al. |
| 5,280,781 A | | 1/1994 | Oku |
| 5,499,632 A | | 3/1996 | Hill et al. |
| 5,524,180 A | | 6/1996 | Wang et al. |
| 5,526,812 A | * | 6/1996 | Dumoulin et al. ........... 600/407 |
| 5,550,953 A | | 8/1996 | Seraji |
| 5,694,142 A | | 12/1997 | Dumoulin et al. |
| 5,762,458 A | | 6/1998 | Wang et al. |
| 5,808,665 A | | 9/1998 | Green |
| 5,831,614 A | | 11/1998 | Tognazzini et al. |
| 5,899,851 A | | 5/1999 | Koninckx |
| 5,935,075 A | | 8/1999 | Casscells |
| 5,963,770 A | | 10/1999 | Eakin |
| 6,007,550 A | | 12/1999 | Wang et al. |
| 6,016,439 A | | 1/2000 | Acker |
| 6,038,467 A | * | 3/2000 | De Bliek et al. ........... 600/424 |
| 6,047,080 A | | 4/2000 | Chen |
| 6,059,718 A | | 5/2000 | Taniguchi et al. |
| 6,063,095 A | | 5/2000 | Wang et al. |
| 6,096,004 A | | 8/2000 | Meglan et al. |
| 6,167,292 A | | 12/2000 | Badano |
| 6,203,493 B1 | | 3/2001 | Ben-Haim |
| 6,246,784 B1 | | 6/2001 | Summers |
| 6,246,898 B1 | | 6/2001 | Vesely |
| 6,332,089 B1 | | 12/2001 | Acker |
| 6,425,865 B1 | * | 7/2002 | Salcudean ............ A61B 8/0875 600/111 |
| 6,466,198 B1 | | 10/2002 | Feinstein |
| 6,468,265 B1 | | 10/2002 | Evans et al. |
| 6,490,467 B1 | | 12/2002 | Bucholz |
| 6,516,421 B1 | | 2/2003 | Peters |
| 6,553,251 B1 | | 4/2003 | Lahdesmaki |
| 6,665,554 B1 | | 12/2003 | Charles |
| 6,690,963 B2 | | 2/2004 | Ben-Haim |
| 6,690,964 B2 | | 2/2004 | Bieger et al. |
| 6,755,797 B1 | | 6/2004 | Stouffer |
| 6,812,842 B2 | | 11/2004 | Dimmer |
| 6,856,827 B2 | | 2/2005 | Seeley et al. |
| 6,899,672 B2 | | 5/2005 | Chin |
| 6,926,709 B2 | | 8/2005 | Beiger et al. |
| 7,180,976 B2 | | 2/2007 | Wink |
| 7,203,277 B2 | | 4/2007 | Birkenbach et al. |
| 7,206,627 B2 | * | 4/2007 | Abovitz ............ A61B 17/3403 600/407 |
| 7,233,820 B2 | | 6/2007 | Gilboa |
| 7,386,339 B2 | | 6/2008 | Strommer et al. |
| 7,594,925 B2 | | 9/2009 | Danek |
| 7,618,371 B2 | | 11/2009 | Younge et al. |
| 7,756,563 B2 | | 7/2010 | Higgins |
| 7,774,044 B2 | | 8/2010 | Sauer et al. |
| 7,850,642 B2 | | 12/2010 | Moll et al. |
| 7,880,739 B2 | | 2/2011 | Long et al. |
| 7,901,348 B2 | | 3/2011 | Soper |
| 7,935,059 B2 | | 5/2011 | Younge et al. |
| 7,963,288 B2 | | 6/2011 | Rosenberg et al. |
| 7,972,298 B2 | | 7/2011 | Wallace et al. |
| 7,974,681 B2 | | 7/2011 | Wallace et al. |
| 7,976,539 B2 | | 7/2011 | Hlavka et al. |
| 8,005,537 B2 | | 8/2011 | Hlavka et al. |
| 8,021,326 B2 | | 9/2011 | Moll et al. |
| 8,041,413 B2 | | 10/2011 | Barbagli et al. |
| 8,050,523 B2 | | 11/2011 | Younge et al. |
| 8,052,621 B2 | | 11/2011 | Wallace et al. |
| 8,052,636 B2 | | 11/2011 | Moll et al. |
| 8,092,397 B2 | | 1/2012 | Wallace et al. |
| 8,108,069 B2 | | 1/2012 | Stahler et al. |
| 8,155,403 B2 | | 4/2012 | Tschirren |
| 8,172,747 B2 | | 5/2012 | Wallace et al. |
| 8,180,114 B2 | | 5/2012 | Nishihara et al. |
| 8,190,238 B2 | | 5/2012 | Moll et al. |
| 8,257,303 B2 | | 9/2012 | Moll et al. |
| 8,285,364 B2 | | 10/2012 | Barbagli et al. |
| 8,290,571 B2 | | 10/2012 | Younge et al. |
| 8,298,135 B2 | | 10/2012 | Ito et al. |
| 8,311,626 B2 | | 11/2012 | Hlavka et al. |
| 8,317,746 B2 | | 11/2012 | Sewell et al. |
| 8,388,538 B2 | | 3/2013 | Younge et al. |
| 8,388,556 B2 | | 3/2013 | Wallace et al. |
| 8,394,054 B2 | | 3/2013 | Wallace et al. |
| 8,409,136 B2 | | 4/2013 | Wallace et al. |
| 8,409,172 B2 | | 4/2013 | Moll et al. |
| 8,409,234 B2 | | 4/2013 | Stahler et al. |
| 8,460,236 B2 | | 6/2013 | Roelle et al. |
| 8,498,691 B2 | | 7/2013 | Moll et al. |
| 8,617,102 B2 | | 12/2013 | Moll et al. |
| 8,716,973 B1 | | 5/2014 | Lammertse |
| 8,718,837 B2 | | 5/2014 | Wang et al. |
| 8,720,448 B2 | | 5/2014 | Reis et al. |
| 8,801,661 B2 | | 8/2014 | Moll et al. |
| 8,821,376 B2 | | 9/2014 | Tolkowsky |
| 8,858,424 B2 | | 10/2014 | Hasegawa |
| 8,926,603 B2 | | 1/2015 | Hlavka et al. |
| 8,929,631 B2 | | 1/2015 | Pfister et al. |
| 8,961,533 B2 | | 2/2015 | Stahler et al. |
| 8,971,597 B2 | | 3/2015 | Zhao et al. |
| 8,974,408 B2 | | 3/2015 | Wallace et al. |
| 9,014,851 B2 | | 4/2015 | Wong et al. |
| 9,084,623 B2 | | 7/2015 | Gomez et al. |
| 9,125,639 B2 | | 9/2015 | Mathis |
| 9,138,129 B2 | | 9/2015 | Diolaiti |
| 9,173,713 B2 | | 11/2015 | Hart et al. |
| 9,183,354 B2 | | 11/2015 | Baker et al. |
| 9,186,046 B2 | | 11/2015 | Ramamurthy et al. |
| 9,241,767 B2 | | 1/2016 | Prisco et al. |
| 9,272,416 B2 | | 3/2016 | Hourtash et al. |
| 9,283,046 B2 | | 3/2016 | Walker et al. |
| 9,289,578 B2 | | 3/2016 | Walker et al. |
| 9,358,076 B2 | | 6/2016 | Moll et al. |
| 9,457,168 B2 | | 10/2016 | Moll et al. |
| 9,459,087 B2 | | 10/2016 | Dunbar |
| 9,498,291 B2 | | 11/2016 | Balaji et al. |
| 9,498,601 B2 | | 11/2016 | Tanner et al. |

(56) References Cited

U.S. PATENT DOCUMENTS

| | | |
|---|---|---|
| 9,503,681 B1 | 11/2016 | Popescu et al. |
| 9,504,604 B2 | 11/2016 | Alvarez |
| 9,561,019 B2 | 2/2017 | Mihailescu et al. |
| 9,561,083 B2 | 2/2017 | Yu et al. |
| 9,566,414 B2 | 2/2017 | Wong et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,770,216 B2 | 9/2017 | Brown et al. |
| 9,788,910 B2 | 10/2017 | Schuh |
| 9,827,061 B2 | 11/2017 | Balaji et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 10,016,900 B1 | 7/2018 | Meyer et al. |
| 10,022,192 B1 | 7/2018 | Ummalaneni |
| 10,028,789 B2 | 7/2018 | Quaid et al. |
| 10,046,140 B2 | 8/2018 | Kokish et al. |
| 10,123,843 B2 | 11/2018 | Wong et al. |
| 10,130,427 B2 | 11/2018 | Tanner et al. |
| 10,136,950 B2 | 11/2018 | Schoenefeld |
| 10,143,526 B2 | 12/2018 | Walker et al. |
| 10,145,747 B1 | 12/2018 | Lin et al. |
| 10,159,532 B1 | 12/2018 | Ummalaneni et al. |
| 10,206,746 B2 | 2/2019 | Walker et al. |
| 10,278,778 B2 | 5/2019 | State |
| 10,285,574 B2 | 5/2019 | Landey et al. |
| 10,299,870 B2 | 5/2019 | Connolly et al. |
| 10,346,976 B2 | 7/2019 | Averbuch et al. |
| 10,482,599 B2 | 11/2019 | Mintz et al. |
| 10,820,954 B2 | 11/2020 | Marsot et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1* | 6/2002 | Bieger et al. ............... 600/300 |
| 2002/0082612 A1 | 6/2002 | Moll et al. |
| 2002/0120188 A1* | 8/2002 | Brock et al. ............... 600/407 |
| 2002/0161280 A1 | 10/2002 | Chatenever et al. |
| 2002/0173878 A1 | 11/2002 | Watanabe |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1* | 3/2004 | Dalton ............................ 359/630 |
| 2004/0072066 A1 | 4/2004 | Cho et al. |
| 2004/0186349 A1 | 9/2004 | Ewers |
| 2004/0249267 A1 | 12/2004 | Gilboa |
| 2004/0263535 A1* | 12/2004 | Birkenbach ............ A61B 6/032 345/629 |
| 2005/0027397 A1 | 2/2005 | Niemeyer |
| 2005/0043718 A1 | 2/2005 | Madhani |
| 2005/0060006 A1 | 3/2005 | Pflueger |
| 2005/0085714 A1* | 4/2005 | Foley ............... A61B 17/1735 600/424 |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |
| 2005/0193451 A1* | 9/2005 | Quistgaard ......... A61B 5/6843 414/1 |
| 2005/0197557 A1 | 9/2005 | Strommer et al. |
| 2005/0222554 A1 | 10/2005 | Wallace et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0058643 A1 | 3/2006 | Florent |
| 2006/0079745 A1 | 4/2006 | Viswanathan et al. |
| 2006/0084860 A1 | 4/2006 | Geiger |
| 2006/0095022 A1 | 5/2006 | Moll et al. |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0200026 A1 | 9/2006 | Wallace et al. |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083098 A1 | 4/2007 | Stern et al. |
| 2007/0083193 A1 | 4/2007 | Werneth |
| 2007/0123748 A1 | 5/2007 | Meglan |
| 2007/0135886 A1 | 6/2007 | Maschke |
| 2007/0138992 A1 | 6/2007 | Prisco et al. |
| 2007/0144298 A1 | 6/2007 | Miller |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0185486 A1 | 8/2007 | Hauck et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0027313 A1 | 1/2008 | Shachar |
| 2008/0027464 A1 | 1/2008 | Moll et al. |
| 2008/0033442 A1 | 2/2008 | Amoit |
| 2008/0071140 A1 | 3/2008 | Gattani |
| 2008/0079421 A1 | 4/2008 | Jensen |
| 2008/0082109 A1 | 4/2008 | Moll et al. |
| 2008/0097465 A1 | 4/2008 | Rollins et al. |
| 2008/0103389 A1 | 5/2008 | Begelman et al. |
| 2008/0108870 A1 | 5/2008 | Wiita et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0140087 A1 | 6/2008 | Barbagli |
| 2008/0147089 A1 | 6/2008 | Loh |
| 2008/0159653 A1 | 7/2008 | Dunki-Jacobs et al. |
| 2008/0161681 A1 | 7/2008 | Hauck |
| 2008/0183064 A1 | 7/2008 | Chandonnet |
| 2008/0183068 A1* | 7/2008 | Carls ............... A61B 5/04001 600/411 |
| 2008/0183073 A1 | 7/2008 | Higgins et al. |
| 2008/0183188 A1* | 7/2008 | Carls et al. ............... 606/130 |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243064 A1 | 10/2008 | Stahler et al. |
| 2008/0243142 A1 | 10/2008 | Gildenberg |
| 2008/0249536 A1 | 10/2008 | Stahler et al. |
| 2008/0262297 A1 | 10/2008 | Gilboa |
| 2008/0262480 A1 | 10/2008 | Stahler et al. |
| 2008/0262513 A1 | 10/2008 | Stahler et al. |
| 2008/0275349 A1 | 11/2008 | Halperin |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0024141 A1 | 1/2009 | Stahler et al. |
| 2009/0030307 A1 | 1/2009 | Govari |
| 2009/0054729 A1 | 2/2009 | Mori |
| 2009/0062602 A1 | 3/2009 | Rosenberg et al. |
| 2009/0076476 A1 | 3/2009 | Barbagli et al. |
| 2009/0138025 A1 | 5/2009 | Stahler et al. |
| 2009/0149867 A1 | 6/2009 | Glozman |
| 2009/0209817 A1 | 8/2009 | Averbuch |
| 2009/0227861 A1 | 9/2009 | Ganatra |

(56) References Cited

U.S. PATENT DOCUMENTS

| | | |
|---|---|---|
| 2009/0228020 A1 | 9/2009 | Wallace et al. |
| 2009/0248036 A1* | 10/2009 | Hoffman et al. ............ 606/130 |
| 2009/0254083 A1 | 10/2009 | Wallace et al. |
| 2009/0259230 A1* | 10/2009 | Khadem ............ A61B 19/5244 606/130 |
| 2009/0259412 A1 | 10/2009 | Brogardh |
| 2009/0262109 A1 | 10/2009 | Markowitz et al. |
| 2009/0292166 A1 | 11/2009 | Ito |
| 2009/0295797 A1 | 12/2009 | Sakaguchi |
| 2009/0322671 A1 | 12/2009 | Scott et al. |
| 2009/0326322 A1 | 12/2009 | Diolaiti |
| 2009/0326556 A1 | 12/2009 | Diolaiti et al. |
| 2010/0008555 A1 | 1/2010 | Trumer |
| 2010/0019890 A1 | 1/2010 | Helmer et al. |
| 2010/0030061 A1 | 2/2010 | Canfield |
| 2010/0039506 A1* | 2/2010 | Sarvestani et al. ............ 348/65 |
| 2010/0041949 A1 | 2/2010 | Tolkowsky |
| 2010/0053151 A1 | 3/2010 | Marti et al. |
| 2010/0054536 A1 | 3/2010 | Huang |
| 2010/0076263 A1 | 3/2010 | Tanaka |
| 2010/0113852 A1 | 5/2010 | Sydora |
| 2010/0121139 A1 | 5/2010 | OuYang |
| 2010/0121269 A1 | 5/2010 | Goldenberg |
| 2010/0125284 A1 | 5/2010 | Tanner et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0204613 A1 | 8/2010 | Rollins et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0295931 A1 | 11/2010 | Schmidt |
| 2010/0298641 A1 | 11/2010 | Tanaka |
| 2010/0328455 A1 | 12/2010 | Nam et al. |
| 2011/0015648 A1 | 1/2011 | Alvarez et al. |
| 2011/0021926 A1 | 1/2011 | Spencer |
| 2011/0054303 A1 | 3/2011 | Barrick |
| 2011/0092808 A1 | 4/2011 | Shachar |
| 2011/0113852 A1 | 5/2011 | Prisco |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0184238 A1 | 7/2011 | Higgins |
| 2011/0196199 A1 | 8/2011 | Donhowe et al. |
| 2011/0234780 A1 | 9/2011 | Ito |
| 2011/0235855 A1 | 9/2011 | Smith |
| 2011/0238010 A1 | 9/2011 | Kirschenman et al. |
| 2011/0238082 A1 | 9/2011 | Wenderow |
| 2011/0238083 A1 | 9/2011 | Moll et al. |
| 2011/0245665 A1 | 10/2011 | Nentwick |
| 2011/0248987 A1* | 10/2011 | Mitchell ............ 345/419 |
| 2011/0249016 A1 | 10/2011 | Zhang |
| 2011/0257480 A1 | 10/2011 | Takahashi |
| 2011/0270273 A1 | 11/2011 | Moll et al. |
| 2011/0276058 A1 | 11/2011 | Choi et al. |
| 2011/0276179 A1 | 11/2011 | Banks et al. |
| 2011/0295247 A1 | 12/2011 | Schlesinger et al. |
| 2011/0295248 A1 | 12/2011 | Wallace et al. |
| 2011/0295267 A1 | 12/2011 | Tanner et al. |
| 2011/0295268 A1 | 12/2011 | Roelle et al. |
| 2011/0306873 A1 | 12/2011 | Shenai et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059392 A1 | 3/2012 | Diolaiti |
| 2012/0062714 A1 | 3/2012 | Liu |
| 2012/0065481 A1 | 3/2012 | Hunter |
| 2012/0069167 A1 | 3/2012 | Liu et al. |
| 2012/0071752 A1 | 3/2012 | Sewell |
| 2012/0071782 A1 | 3/2012 | Patil et al. |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0082351 A1 | 4/2012 | Higgins |
| 2012/0103123 A1 | 5/2012 | McInroy et al. |
| 2012/0116253 A1 | 5/2012 | Wallace et al. |
| 2012/0120305 A1 | 5/2012 | Takahashi |
| 2012/0158011 A1 | 6/2012 | Sandhu |
| 2012/0165656 A1 | 6/2012 | Montag |
| 2012/0191079 A1 | 7/2012 | Moll et al. |
| 2012/0203067 A1 | 8/2012 | Higgins et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0253276 A1 | 10/2012 | Govari et al. |
| 2012/0289777 A1 | 11/2012 | Chopra |
| 2012/0289783 A1 | 11/2012 | Duindam et al. |
| 2012/0296161 A1 | 11/2012 | Wallace et al. |
| 2012/0302869 A1 | 11/2012 | Koyrakh |
| 2012/0314022 A1 | 12/2012 | Jo |
| 2013/0018306 A1 | 1/2013 | Ludwin |
| 2013/0060146 A1* | 3/2013 | Yang ............ A61B 5/055 600/476 |
| 2013/0072787 A1 | 3/2013 | Wallace et al. |
| 2013/0144116 A1 | 6/2013 | Cooper et al. |
| 2013/0165854 A1 | 6/2013 | Sandhu et al. |
| 2013/0165945 A9 | 6/2013 | Roelle |
| 2013/0190741 A1 | 7/2013 | Moll et al. |
| 2013/0204124 A1 | 8/2013 | Duindam |
| 2013/0225942 A1 | 8/2013 | Holsing |
| 2013/0243153 A1 | 9/2013 | Sra |
| 2013/0245375 A1 | 9/2013 | DiMaio et al. |
| 2013/0246334 A1 | 9/2013 | Ahuja |
| 2013/0259315 A1 | 10/2013 | Angot et al. |
| 2013/0303892 A1 | 11/2013 | Zhao |
| 2013/0317519 A1 | 11/2013 | Romo et al. |
| 2013/0345718 A1 | 12/2013 | Crawford |
| 2014/0058406 A1 | 2/2014 | Tsekos |
| 2014/0072192 A1 | 3/2014 | Reiner |
| 2014/0107390 A1 | 4/2014 | Brown |
| 2014/0107666 A1 | 4/2014 | Madhani |
| 2014/0111457 A1 | 4/2014 | Briden et al. |
| 2014/0114180 A1 | 4/2014 | Jain |
| 2014/0148808 A1 | 4/2014 | Inkpen et al. |
| 2014/0142591 A1 | 5/2014 | Alvarez et al. |
| 2014/0180063 A1 | 6/2014 | Zhao |
| 2014/0222204 A1 | 8/2014 | Kawashima |
| 2014/0235943 A1 | 8/2014 | Paris |
| 2014/0243849 A1 | 8/2014 | Saglam |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276392 A1 | 9/2014 | Wong et al. |
| 2014/0276594 A1 | 9/2014 | Tanner et al. |
| 2014/0276933 A1 | 9/2014 | Hart et al. |
| 2014/0276937 A1 | 9/2014 | Wong et al. |
| 2014/0276938 A1 | 9/2014 | Hsu et al. |
| 2014/0277333 A1 | 9/2014 | Lewis et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357953 A1 | 12/2014 | Roelle et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2014/0379000 A1 | 12/2014 | Romo et al. |
| 2015/0018622 A1 | 1/2015 | Tesar et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0101442 A1 | 4/2015 | Romo |
| 2015/0105747 A1 | 4/2015 | Rollins et al. |
| 2015/0119638 A1 | 4/2015 | Yu et al. |
| 2015/0141808 A1 | 5/2015 | Elhawary |

(56) References Cited

U.S. PATENT DOCUMENTS

| | | |
|---|---|---|
| 2015/0141858 A1 | 5/2015 | Razavi |
| 2015/0142013 A1 | 5/2015 | Tanner et al. |
| 2015/0157191 A1 | 6/2015 | Phee et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0224845 A1 | 8/2015 | Anderson et al. |
| 2015/0255782 A1 | 9/2015 | Kim et al. |
| 2015/0265087 A1 | 9/2015 | Park |
| 2015/0265368 A1 | 9/2015 | Chopra |
| 2015/0265807 A1 | 9/2015 | Park et al. |
| 2015/0275986 A1 | 10/2015 | Cooper |
| 2015/0287192 A1 | 10/2015 | Sasaki |
| 2015/0290454 A1 | 10/2015 | Tyler et al. |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2015/0375399 A1 | 12/2015 | Chiu et al. |
| 2016/0000302 A1 | 1/2016 | Brown |
| 2016/0000414 A1 | 1/2016 | Brown |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0026253 A1 | 1/2016 | Bradski et al. |
| 2016/0059412 A1 | 3/2016 | Oleynik |
| 2016/0098095 A1 | 4/2016 | Gonzalez-Banos et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0213436 A1 | 7/2016 | Inoue |
| 2016/0213884 A1 | 7/2016 | Park |
| 2016/0228032 A1 | 8/2016 | Walker et al. |
| 2016/0235495 A1 | 8/2016 | Wallace et al. |
| 2016/0256069 A1 | 9/2016 | Jenkins |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1 | 11/2016 | Esterberg et al. |
| 2016/0331469 A1 | 11/2016 | Hall et al. |
| 2016/0360947 A1 | 12/2016 | Iida |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0065364 A1 | 3/2017 | Schuh et al. |
| 2017/0065365 A1 | 3/2017 | Schuh |
| 2017/0079725 A1 | 3/2017 | Hoffman |
| 2017/0079726 A1 | 3/2017 | Hoffman |
| 2017/0086929 A1 | 3/2017 | Moll et al. |
| 2017/0100199 A1 | 4/2017 | Yu et al. |
| 2017/0113019 A1 | 4/2017 | Wong et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0143429 A1 | 5/2017 | Richmond et al. |
| 2017/0165011 A1 | 6/2017 | Bovay et al. |
| 2017/0172664 A1 | 6/2017 | Weingarten et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0215978 A1 | 8/2017 | Wallace et al. |
| 2017/0238807 A9 | 8/2017 | Veritkov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360418 A1 | 12/2017 | Wong et al. |
| 2017/0360508 A1 | 12/2017 | Germain et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0055583 A1 | 3/2018 | Schuh et al. |
| 2018/0078321 A1 | 3/2018 | Liao |
| 2018/0079090 A1 | 3/2018 | Koenig et al. |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0184988 A1 | 7/2018 | Walker et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083183 A1 | 3/2019 | Moll et al. |
| 2019/0086349 A1 | 3/2019 | Nelson |
| 2019/0090969 A1 | 3/2019 | Jarc et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0117176 A1 | 4/2019 | Walker et al. |
| 2019/0117203 A1 | 4/2019 | Wong et al. |
| 2019/0151148 A1 | 4/2019 | Alvarez et al. |
| 2019/0125164 A1 | 5/2019 | Roelle et al. |
| 2019/0142519 A1 | 5/2019 | Siemionow et al. |
| 2019/0151032 A1 | 5/2019 | Mustufa et al. |
| 2019/0167361 A1 | 6/2019 | Walker et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |

(56) References Cited

U.S. PATENT DOCUMENTS

| | | |
|---|---|---|
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0371012 A1 | 12/2019 | Flexman |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0345432 A1 | 11/2020 | Walker |
| 2020/0352420 A1 | 11/2020 | Graetzel |
| 2020/0360183 A1 | 11/2020 | Alvarez |
| 2020/0360659 A1 | 11/2020 | Wong |
| 2020/0367726 A1 | 11/2020 | Landey et al. |
| 2020/0367981 A1 | 11/2020 | Ho et al. |
| 2020/0375678 A1 | 12/2020 | Wallace |

FOREIGN PATENT DOCUMENTS

| | | |
|---|---|---|
| CN | 102316817 | 1/2012 |
| CN | 102458295 | 5/2012 |
| CN | 102946801 | 2/2013 |
| CN | 102973317 | 3/2013 |
| CN | 103705307 | 4/2014 |
| CN | 103735313 | 4/2014 |
| CN | 103813748 | 5/2014 |
| CN | 104758066 | 7/2015 |
| CN | 105559850 | 5/2016 |
| CN | 105559886 | 5/2016 |
| CN | 105611881 | 5/2016 |
| CN | 106455908 | 2/2017 |
| CN | 106821498 | 6/2017 |
| CN | 104931059 | 9/2018 |
| EP | 1 800 593 | 6/2007 |
| EP | 1 109 497 | 5/2009 |
| EP | 2 158 834 | 3/2010 |
| EP | 3 025 630 | 6/2019 |
| KR | 10-2014-0009359 | 1/2014 |
| KR | 10-1713676 B1 | 3/2017 |
| RU | 2569699 C2 | 11/2015 |
| WO | WO 05/087128 | 9/2005 |
| WO | WO 09/097461 | 6/2007 |
| WO | WO 08/049088 | 4/2008 |
| WO | WO 10/025522 | 3/2010 |
| WO | WO-2013040498 A1 | 3/2013 |
| WO | WO 15/089013 | 6/2015 |
| WO | WO 16/077419 | 5/2016 |
| WO | WO 16/203727 | 12/2016 |
| WO | WO 17/036774 | 3/2017 |
| WO | WO 17/048194 | 3/2017 |
| WO | WO 17/066108 | 4/2017 |
| WO | WO 17/146890 | 8/2017 |
| WO | WO 17/167754 | 10/2017 |
| WO | WO 17/214243 | 12/2017 |

OTHER PUBLICATIONS

Solheim et al., "Navigated resection of giant intracranial meningiomas based on intraoperative 3D ultrasound," May 14, 2009, Acta Neurochir, 151:1143-1151.*
"Point Cloud," Sep. 10, 2010, Wikipedia.*
European search report and search opinion dated Aug. 24, 2015 for EP Application No. 12832283.1.
International search report and written opinion dated Feb. 5, 2013 for PCT/US2012/055634.
Nikou, et al. Augmented reality imaging technology for orthopaedic surgery. Operative Techniques in Orthopaedics 10.1 (2000): 82-86.
Office action dated Mar. 17, 2015 for U.S. Appl. No. 13/618,915.
Office action dated May 11, 2016 for U.S. Appl. No. 13/618,915.
Office action dated May 24, 2017 for U.S. Appl. No. 13/618,915.
Office action dated Aug. 14, 2014 for U.S. Appl. No. 13/618,915.
Office action dated Oct. 14, 2016 for U.S. Appl. No. 13/618,915.
Notice of allowance dated Nov. 8, 2017 for U.S. Appl. No. 13/618,915.
Notice of allowance dated Nov. 22, 2017 for U.S. Appl. No. 13/618,915.
Ciuti et al., 2012, Intra-operative monocular 30 reconstruction for image-guided navigation in active locomotion capsule endoscopy. Biomedical Robotics and Biomechatronics (Biorob), 4th IEEE Ras & Embs International Conference on IEEE.
Fallavollita et al., 2010, Acquiring multiview C-arm images to assist cardiac ablation procedures, EURASIP Journal on Image and Video Processing, vol. 2010, Article ID 871408, pp. 1-10.
Kumar et al., 2014, Stereoscopic visualization of laparoscope image using depth information from 3D model, Computer methods and programs in biomedicine 113(3):862-868.
Livatino et al., 2015, Stereoscopic visualization and 3-D technologies in medical endoscopic teleoperation, IEEE.
Luo et al., 2010, Modified hybrid bronchoscope tracking based on sequential monte carlo sampler: Dynamic phantom validation, Asian Conference on Computer Vision. Springer, Berlin, Heidelberg.
Mourgues et al., 2002, Flexible calibration of actuated stereoscopic endoscope for overlay inrobot assisted surgery, International Con-

(56) References Cited

OTHER PUBLICATIONS ference on Medical Image Computing and Computer-Assisted Intervention. Springer, Berlin, Heidelberg.
Nadeem et al., 2016, Depth Reconstruction and Computer-Aided Polyp Detection in Optical Colonoscopy Video Frames, arXiv preprint arXiv:1609.01329.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813.
Song et al., 2012, Autonomous and stable tracking of endoscope instrument tools with monocular camera, Advanced Intelligent Mechatronics (AIM), 2012 IEEE-ASME International Conference on. IEEE.
Verdaasdonk et al., Jan. 23, 2013, Effect of microsecond pulse length and tip shape on explosive bubble formation of 2.78 iLtr Er,Cr:YSGG and 2.94 iLtrm Er:YAG laser, Proceeings fo SPIE, vol. 8221, 12.
Yip et al., 2012, Tissue tracking and registration for image-guided surgery, IEEE transactions on medical imaging 31(11):2169-2182.
Zhou et al., 2010, Synthesis of stereoscopic views from monocular endoscopic videos, Computer Vision and Pattern Recognition Workshops (CVPRW), 2010 IEEE Computer Society Conference on IEEE.
Haigron et al., 2004, Depth-map-based scene analysis for activew navigation in virtual angioscopy, IEEE Transactions on Medical Imaging; 23(11):1380-1390.
Kiraly et al, 2002, Three-dimensional Human Airway Segmentation Methods for Clinical Virtual Bronchoscopy, Acad Radiol, 9:1153-1168.
Kiraly et al., Sep. 2004, Three-dimensional path planning for virtual bronchoscopy, IEEE Transactions on Medical Imaging, 23(9):1365-1379.
Solomon et al., Dec. 2000, Three-dimensional CT- Guided Bronchoscopy With a Real-Time Electromagnetic Position Sensor a Comparison of Two Image Registration Methods, Chest, 118(6):1783-1787.
Konen et al., 1998, The VN-project: endoscopic image processing for neurosurgery, Computer Aided Surgery, 3:1-6.
Mayo Clinic, Robotic Surgery, https://www.mayoclinic.org/tests-procedures/robotic-surgery/about/pac-20394974?p=1, downloaded from the internet on Jul. 12, 2018, 2 pp.
Shi et al., Sep. 14-18, 2014, Simultaneous catheter and environment modeling for trans-catheter aortic valve implantation, IEEE/RSJ International Conference on Intelligent Robots and Systems, pp. 2024-2029.
Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.
Wilson et al., 2008, a buyer's guide to electromagnetic tracking systems for clinical applications, Proc. of SPCI, 6918:69182B-1 p. 6918B-11.
Al-Ahmad et al., dated 2005, Early experience with a computerized robotically controlled catheter system, Journal of Interventional Cardiac Electrophysiology, 12:199-202.
Bell et al., 2014, Six DOF motion estimation for teleoperated flexible endoscopes using optical flow: a comparative study, IEEE International Conference on Robotis and Automation,.
Gutierrez et al., Mar. 2008, A practical global distortion correction method for an image intensifier based x-ray fluoroscopy system, Med. Phys, 35(3):997-1007.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Marrouche et al., dated May 6, 2005, AB32-1, Preliminary human experience using a novel robotic catheter remote control, Heart Rhythm, 2(5):S63.
Oh et al., dated May 2005, P5-75, Novel robotic catheter remote control system: safety and accuracy in delivering RF Lesions in all 4 cardiac chambers, Heart Rhythm, 2(5):5277-5278.
Reddy et al., May 2005, P1-53. Porcine pulmonary vein ablation using a novel robotic catheter control system and real-time integration of CT imaging with electroanatomical mapping, Hearth Rhythm, 2(5):S121.
Ren et al., 2011, Multisensor data fusion in an integrated tracking system for endoscopic surgery, IEEE Transactions on Information Technology in Biomedicine, 16(1):106-111.
Slepian, dated 2010, Robotic Catheter Intervention: the Hansen Medical Sensei Robot Catheter System, PowerPoint presentation, 28 pp.

\* cited by examiner

SYSTEM AND METHOD FOR DISPLAYING ANATOMY AND DEVICES ON A MOVABLE DISPLAY

CROSS-REFERENCE

1. This application claims the benefit of U.S. Provisional Application No. 61/829,078 filed May 30, 2013.

BACKGROUND OF THE INVENTION

1. Field of the Invention

The invention relates generally to the diagnosis and treatment of disorders using minimally invasive techniques. In many minimally invasive procedures very small devices are manipulated within the patient's body under visualization from a live imaging source like ultrasound, fluoroscopy, or endoscopy. Live imaging in a minimally invasive procedure may be supplemented or replaced by displaying the position of a sensored medical device within a stored image of the patient anatomy.

Many minimally invasive procedures are conducted in expensive settings by specialized physicians. Often small, percutaneous medical devices are visualized during the procedure by using live fluoroscopic or ultrasonic imaging. While the live imaging provides a real-time image of anatomy, it has many drawbacks:

Time spent in an imaging suite is expensive and raises the cost of many minimally invasive medical procedures.

Ionizing radiation used to create the fluoroscopic image is dangerous to the patient, physician, and assistants.

Needles, Guidewires, and other small devices may be difficult to locate within the live two-dimensional image. These devices may be too small to see clearly in fluoroscopic images. In ultrasound images, these devices may be difficult to locate when they are outside of the ultrasonic imaging plane or they may reflect a diffused, ambiguous image when they are within the ultrasonic imaging plane.

The fluoroscopic and ultrasonic images are two-dimensional and do not provide determinant information about motion of the medical device and three-dimensional anatomical structures.

During a typical minimally invasive procedure the physician must look away from the patient and his or her hands to see the display showing the live image. Additionally, the frame of reference for the live image is typically misaligned from the frames of reference for the physician, the tool and the patient. This presents a challenging situation for the physician who must compensate for differences in these frames of reference. For instance, when the physician inserts a device into the patient by moving his hands from left to right, the fluoroscopic image of the device moves towards the top of the display. Ultrasonic images can be even more confounding in that the frame of reference for the ultrasound image is based on the position and orientation of the ultrasound probe which is frequently moving during imaging. The physician must compensate for the misalignment of the coordinate systems for the respective frames of reference while also concentrating on achieving the goals of the minimally invasive procedure. The physician's need to look away from the patient and his or her instrument creates an ergonomic challenge in addition to this mental challenge. As a result the completion of minimally invasive procedures becomes delayed, increasing the procedure cost.

Prior to a minimally invasive catheter procedure, patients often have an anatomical image created using CT or MR imaging systems commercially provided by companies like Philips, Siemens, General Electric, and Toshiba. The anatomical images can be processed, or "segmented," into three-dimensional representations of the anatomy of interest. Individual organs, muscles and vasculature can be visually separated from other anatomy for even clearer viewing of regions of interest. In this invention the three-dimensional pre-procedure images may be used instead of or in addition to live imaging for navigation during the procedure because the position and orientation of the medical device can be sensed in real-time. For example, navigation systems provided by Medtronic, GE, and Stryker sense the positions of medical devices within the patient's body and present the sensed position data in a pre-procedural image of the patient's anatomy. These navigation systems provide a supplement or replacement to fluoroscopic imaging so that the physician may conduct a minimally invasive procedure within the patient's body using little or no X-ray. However, the navigation systems do not provide a means for making the physician's hand motions on the medical device match the motions of the device displayed in the image of the anatomy on the display. In order to make minimally invasive procedures easy and intuitive, the coordinate systems of the patient, the device, the display, and the physician's hands must be unified.

Minimally invasive procedures where a medical device is inserted into the body are especially well suited for a system that provides navigation assistance by unifying the physician, patient, display, and device coordinate systems. These procedures usually employ devices that are navigated through the body to small anatomical targets. For example, to obtain a tissue biopsy of a prostate, a physician may insert a small catheter through the urethra into the bladder. The urethral catheter provides an ideal location for the placement of sensors that can be used by software to match the live three-dimensional shape of the urethra to the stored three-dimensional shape of the urethra in the pre-operative image set. This "registration" of the real-time position of the patient's soft tissue to the pre-operative image of the same tissue allows the tissue and adjacent tissue structures to be accessed using the pre-operative images. Then a biopsy needle may be inserted into biopsy targets within the prostate by a physician who is navigating the needle using a three-dimensional image of the prostate. Once target tissue is reached with a needle, it may be treated directly with therapies like RF ablation, cryo-therapy, brachy-therapy or chemo-embolozation. Similar use of the invention may be made for other tissues like breast, liver, lung Endoscopic device use may similarly be improved by displaying an anatomical image that is aligned to the patient. Prior to inserting the endoscope, it is difficult to know the exact locations of anatomical structures within the body. After the endoscope is inserted, the external references of the patient's body are lost. Displaying an anatomical image that is aligned to the patient's body provides context by unifying the external view of the patient with the internal view of the anatomy, allowing the physician to choose optimal placement of access ports and improving the ability access desired anatomy quickly and directly.

Robotic surgical procedures may be improved to displaying the projected workspaces of robotic devices on an anatomical image that is aligned to the patient. The projected path, workspace, and collision space of robotic devices may be overlaid on the anatomical image and viewed from different perspectives by moving the display, allowing the user to optimize the placement of the devices in the patients body for reaching specific target anatomies.

The present invention improves the ease and reliability of visualizing anatomy within a patient by providing a system for displaying the device and patient anatomy in a substantially aligned manner.

2. Description of Background Art

Relevant references include US 2010/295931; US2010/053151; US2010/039506; US2009/322671; U.S. Pat. Nos. 7,880,739; 7,203,277; 5,808,665; 7,774,044; 5,134,390; 6,038,467; and Nikou C, DiGioia A M, Blackwell M, et al. Augmented reality imaging technology for orthopaedic surgery. Operative Techniques in Orthopaedics. 2000; 10:82-86

SUMMARY OF THE INVENTION

The invention comprises a virtual window system that creates a visual coherency between the patient's anatomical images and the actual patient by aligning the image on the display to the patient and then presenting the image to the user in a way that feels as if the user is looking directly into the patient through the display. The invention is designed to also display medical devices, such as a biopsy needle. The invention makes the anatomy and the motion of the minimally invasive medical device in the display match the motion of the physician's hands by substantially unifying the coordinate systems of the patient, the medical device, the display, and the physician's hands. The invention creates a visual coherency between the motion of the medical device in the image and the motion of the physician's hands manipulating the device. This invention also creates a visual coherency between the motion of the image in the display and the motion of the display. For example, the invention shows the image of the anatomy, the projected path of the biopsy needle, and the actual location of the tip of the biopsy needle in a single image that is shown on a display over the patient in substantial alignment to the patient's actual anatomy.

Embodiments of the invention possess inventive design elements that provide excellent user ergonomics and increase the functional anatomical workspace of the virtual window surgical system. Coupling the position and orientation of the display to the image allows the image to remain aligned to the patient for various positions and orientations of the display. To improve the ergonomics and workspace of the system, the knowledge of the general position of the user relative to the patient is leveraged to slightly bias the image position to an optimized position. For example, if the user is on the left side of the patient, the image may be angled fifteen degrees away from the user so that when the display is angled fifteen degrees toward the user, the image will appear flat relative to the patient. Practice has shown that the intuitive benefits to the user of an aligned image may still be captured when small angular offsets are in place, with offsets of 30 degrees being the well-tolerated limit in many procedures. The system uses the knowledge of the user's position to bias the display toward more comfortable positions. The knowledge of the user's position may be input to the system by the user, inferred by the system using the position of the display, or sensed by the system using position or contact devices on the system. To further increase the workspace of the system, this invention allows for decoupling the relationship to reposition the display independently of the image. For instance, an aligned display may interfere with other equipment during some portion of the procedure and it may be desirable to reposition the display slightly to relieve the interference. Additionally this invention allows for a scaled coupling for improved ergonomics. For instance, moving the display with a unity ratio may cause the display to interfere with other equipment during some portion of the procedure or may make the screen difficult to view. Up to a 1.5:1 scale may be used to optimize the ergonomics of the system while maintaining the visual coherency between the patient and the image. It should be noted that the display may be repositioned along multiple axes and in multiple directions and that the scaling may be different for different axes and directions. For example, the scaling may be unity in the translational axes and 1.3:1 in the rotational axes.

Additionally this invention provides a movable support structure to hold a display directly in front of the physician, between the physician and the patient. Ideally the images are presented in a fashion such that the images are substantially aligned with the patient. This invention details the methods and techniques needed to align the images to the patient. Many embodiments utilize a display that is mounted on a movable support structure that allows for the display to be positioned between the patient and the physician. The range of motion of the support structure and the degrees of freedom enable a wide range of display positions and orientations. In one embodiment, the patient is lying on an exam table with the physician standing by the patient's side. The support structure allows the display to be brought over the patient. The physician can move and orient the display so the display is located roughly between the physician and the patient. Providing a display over the operative area of the patient allows the physician to perform minimally invasive procedures with needles, Guidewires, and catheters as if the physician were performing open surgery by looking directly into the patient.

Techniques are also disclosed to track the position of the display, the imaging source, the patient, and the medical device. Tracking individual elements of the system allows the image to be aligned with the patient and constantly updated to accommodate for a moving patient, moving medical device, or moving display.

A live image of the patient anatomy may also be shown on a display located over the patient. Sensors track the position and orientation of the display screen and the imaging source so that the position and orientation of the display screen may control position and orientation of the imaging source, keeping the anatomical image, the medical device image, and the patient substantially co-aligned. Alternatively, sensors track the position and orientation of the display screen and the imaging source so that the position and orientation of the imaging source may control position and orientation of the display screen, to keep the anatomical image, the display screen, the medical device image, and the patient substantially co-aligned. The live image may be supplemented with other anatomical images from live or static sources that are sensored, registered, and displayed in the same substantially co-aligned manner on the display screen. For example, a live endoscopic image may be superimposed over a three-dimensional image of the prostate derived from a pre-operative MR scan. As the physician moves the display to view the three-dimensional image from different angles, the endoscope may be remotely automatically repositioned so that the live image viewing position matches the viewing position of the three-dimensional image.

All embodiments create a coupling between the image position and orientation and the position and orientation of a secondary system component. This invention improves the workspace of the system by providing an input device to temporarily decouple the relationship to reposition the display or secondary system component for improved workspace. Additionally, this invention improves the ergonomics by allowing for a scaling factor between the coupled display and secondary system component.

In another embodiment the system comprises a processor further adapted to receive image data for the patient's anatomy. Such image data may be a static image obtained by MRI, ultrasound, X-ray, computed tomography or fluoroscopic imaging modalities. The image data can also be a live fluoroscopic image collected in real-time. The system can further track patient position by one or more of the following: fiducial markers, live imaging data, optical sensors, or electromagnetic sensors. The processor is also further adapted to receive position data from a tool, which is tracked by electromagnetic sensors. The display is held by a support arm having at least one degree of freedom, wherein the members and joints of the support arm may be operatively coupled to counterbalance springs or weights. The processor is further adapted to receive position data of the display, which is tracked by one or more of the following: optical tracking, electromagnetic sensors, or encoded joints of the support arm. The processor processes the various position data and image data to display an image of the patient's anatomy substantially aligned with the patient's actual anatomy superimposed with the position of any device being tracked. The processor is also adapted to direct any live imaging equipment to ensure proper functioning of the system. When used in a surgical setting the invention may be located in the surgical field and may also comprise a sterile drape for the display to protect the integrity of the surgical field.

In one embodiment, a live image of the patient anatomy is shown on a repositionable display screen located over the patient. The physician can move the display over the patient while sensors track the motion of the display so that the image shown on the display screen may be periodically or constantly updated to show the medical device, and the patient anatomy substantially aligned with the patient from the perspective of the user with a slight angular bias toward the user. The position of the user relative to the patient may be entered by the user at the start of the procedure by touching a button on the display labeled "patient left," "patient right," "patient head," or "patient feet." In this manner, the image shown on the display provides a view of the medical device and patient anatomy that is intuitive, ergonomic, and allows for easy navigation of the medical device within the patient anatomy shown on the display screen. While the image of the anatomy is frequently based on a pre-operative image, a live image may be supplemented with other anatomical images from live or static sources which are sensored, registered, and displayed in the same substantially co-aligned manner on the display screen.

In additional embodiments, a sensor on the medical device provides position and orientation data of the device to a data processor. A sensor on the patient provides position and orientation data of the patient to the processor, and sensors on the display screen provide the viewing position and orientation of the display screen to the processor. With data from the medical device, the patient, and the display, the processor unifies the three coordinate systems so that the image shown on the display screen substantially matches the position of the patient anatomy. Adjustments to the display position over the patient result in similar changes to the position of the image in the display: changing the position of the display changes the view of the image on the display screen. For example, the user may change the angle of the display to change the angle of the apparent image on the display screen or may translate the display to pan the image in the display along the patient to show different anatomy. Aligning the positions of the shown image and the patient anatomy helps coordinate the physician's control of the medical device.

Elements of both embodiments may be combined to display preoperative and intra-operative anatomical images within the same procedure. In both embodiments, the invention provides a virtual window into the patient where the physician may view the anatomy and navigate the surgical device in substantial alignment with the patient. For example, sensored endoscope may be shown relative to the aligned anatomical image. An anatomical target may be chosen and marked on the image. As sensored medical devices are moved to different potential access points on the body, the ability to reach the anatomical target may be shown by projecting the path of the device to the target and presenting a positive indication when the path to the anatomical target is uninterrupted. Similar real-time updates may be used to assist in quickly choosing access points for minimally invasive devices by showing whether adjacent medical devices will collide with each other, external anatomy, or internal anatomy as different potential access points on the body are selected by moving the medical device to those access points.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 1:
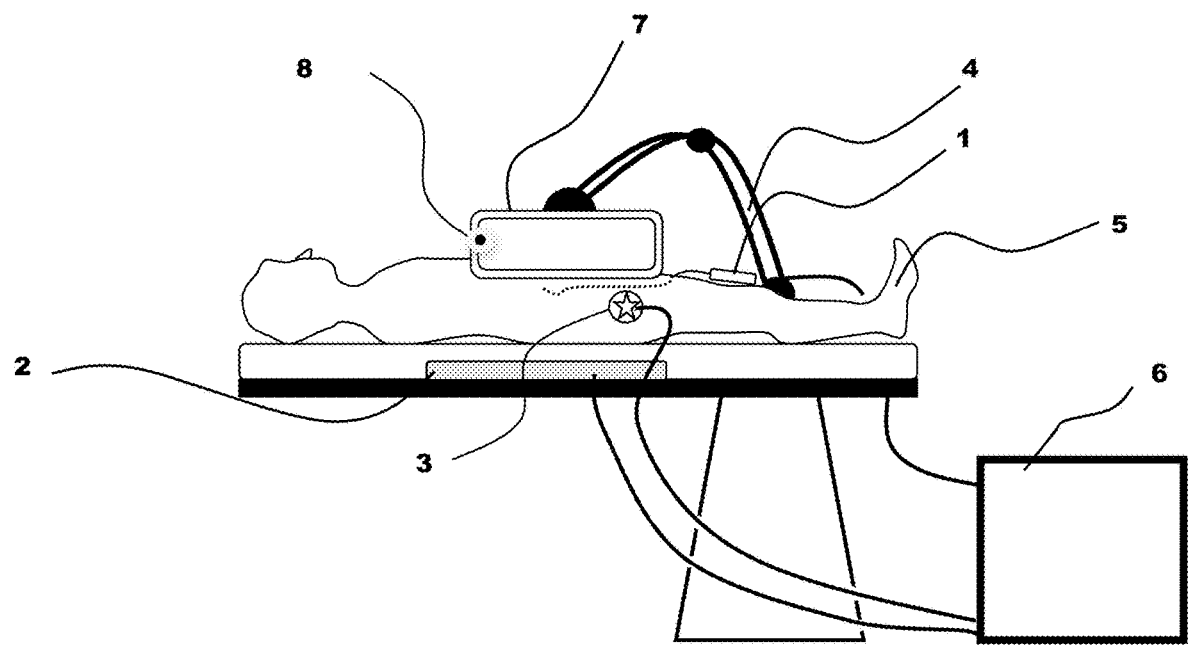
FIG. 1 is a side diagrammatic view of a system for displaying a substantially co-aligned anatomical image with a sensored medical device over a patient's anatomy.
Figure 2:
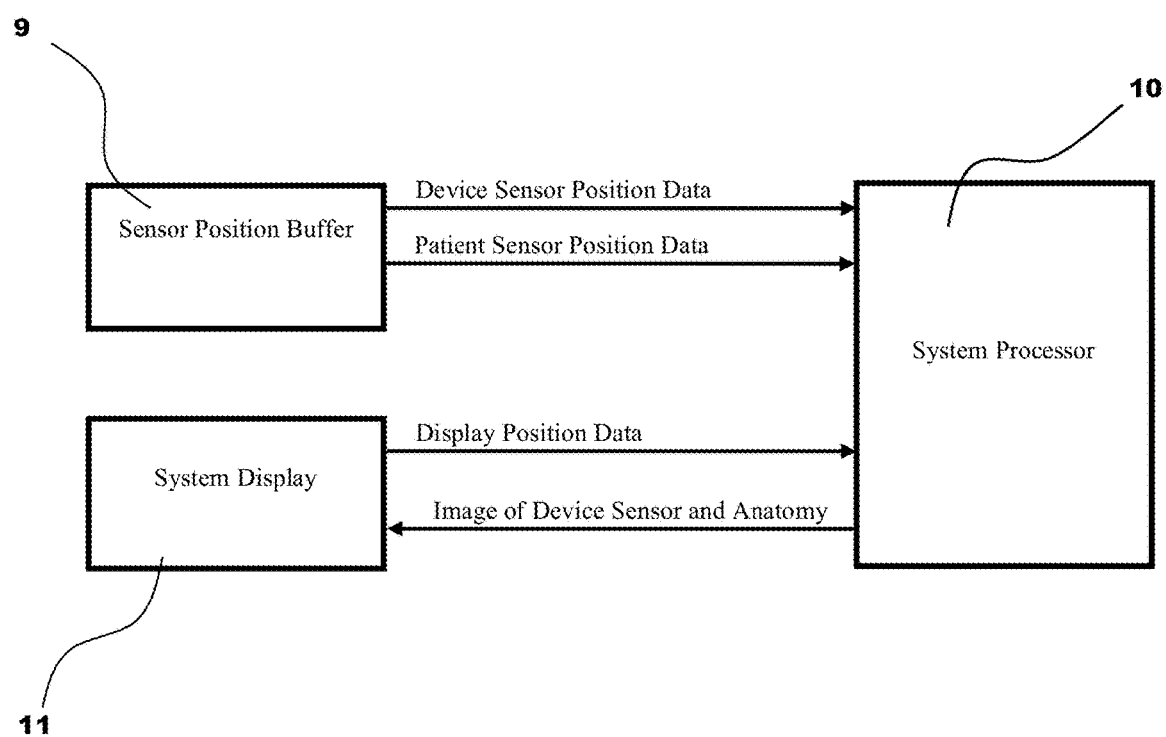
FIG. 2 is a block diagram showing data flow for the system in FIG. 1.

FIGS. 1-2 describe an embodiment for navigating a minimally invasive medical device within the patient using an acquired three-dimensional anatomical image shown in a display 7 that is substantially aligned to the patient anatomy. A sterile cover may be used to separate the display from the sterile operating field and the sterile cover may incorporate a conductive film to provide a sterile touch interface for a capacitive touch screen display. The sterile display cover may be a flexible, clear drape made of plastic like polyethylene or polyurethane film, a rigid plate made of clear plastic like polycarbonate or acrylic, or a combination of both flexible and rigid plastics. The display is preferably a light-weight, flat LCD display provided by manufacturers like LG Display, Philips, and Innolux or a light-weight, flat OLED display provided by manufacturers like Samsung and Sony. A prime example of such a display would be the NEC TFT color LCD module which provides a usable viewing angle of 85° in all directions. In FIG. 1, the position of the medical device within the patient 5 is provided by an electromagnetic coil sensor located on the distal elongated section of the medical device 1. The position of the sensor is derived through an electromagnetic transmitter 2 similar to those transmitters supplied commercially by NDI and Ascension Technology Corporation. Alternatively, the position of the medical device may be derived from an optical fiber position sensor like that supplied by Luna Innovations. A similar patient reference sensor 3 is placed on the patient in a reliably stable position like the outcropping of the pelvic bone, sternum or clavicle. The reference sensor or sensors provide frequently updated data describing the position of the patient anatomy in the same coordinate system as the medical device sensor. The patch holding the patient sensor may be placed on the patient before the patient's anatomy of interest is imaged and the patch may contain known X-ray visible materials such as tungsten, platinum-iridium, platinum, barium sulfide or iodine and MR visible materials such as gadolinium or vitamin E. The patch is visible within the image of the anatomy and therefore the patient reference sensor 3 can be registered to the three dimensional anatomical image. Position data from the sensor in the medical device 1 and patient reference sensor 3 and display support arm 4 are sent to the system processor 6. The local coordinate systems of the medical device sensor 1 and display 7 may undergo a coordinate system transformation in the system processor so that the positions of the device sensor, patient sensor, and display may be evaluated in a single world coordinate system. Display 7 has a user input button 8. FIG. 2 shows the flow of sensor position data from the sensor buffer 9 to the system processor 10 where the position sensor data is used by the processor to place an icon of the medical device into the three-dimensional patient anatomy image for display through the system display 11. The system processor is a standard computing system like those supplied by Dell or Hewlett Packard running an operating system like Windows or Linux. Position data from the system display and support arm is likewise used by the system processor to orient the image on the screen so that the image, based on display position data from the display 7 and support arm 4 and patient position data from the patient reference sensor 3, is substantially aligned with the patient anatomy. Display position data may also be used to modify the image in the display, for example zooming or clipping the image as the display moves closer to the patient. Other image modifications may include changing transparency, removing layers, removing anatomical structures, or changing colors. Additionally, scaling of the image in discrete steps or image modifications may be done via a touch sensitive surface on the display.

Figure 3:
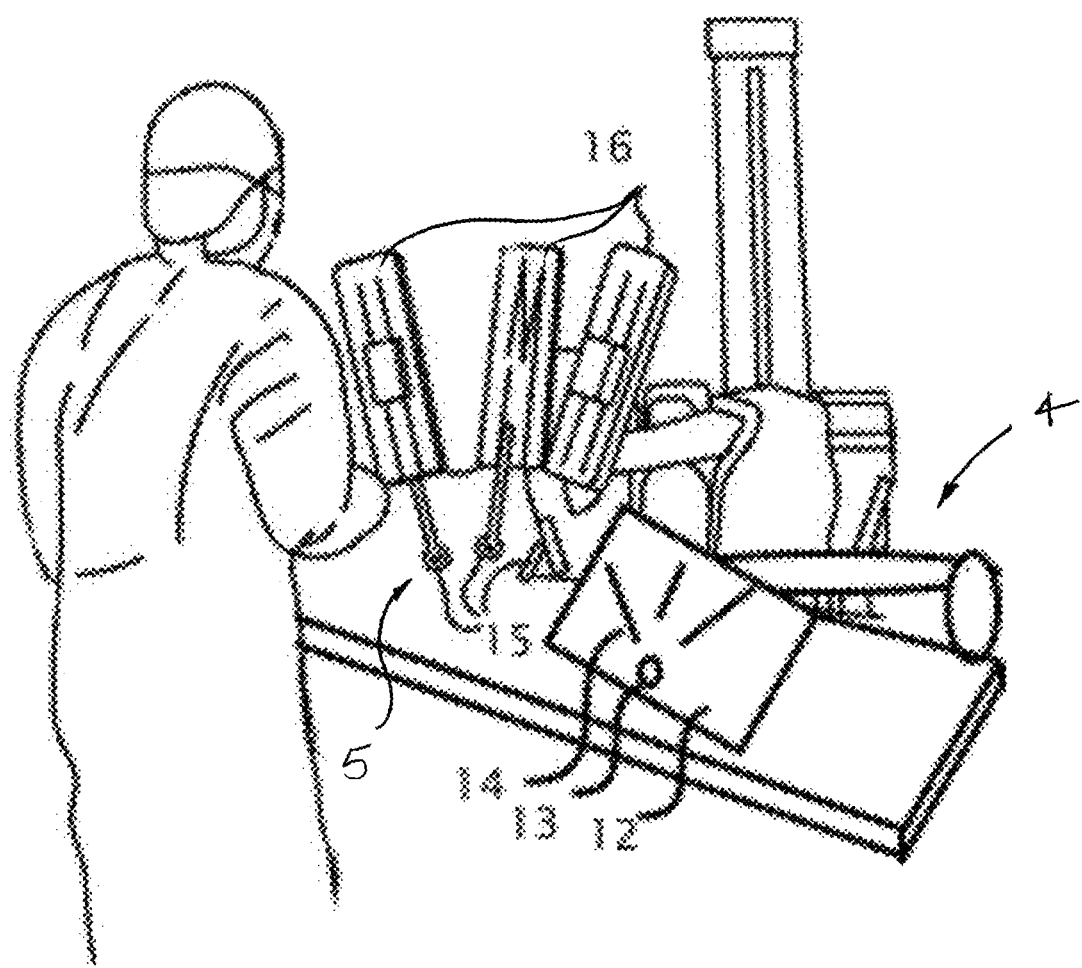
FIG. 3 is an isometric view of an embodiment of the display and support arm positioned next to the patient table with the projected workspace of a robotic surgical device overlaid on the anatomy in the display.

FIG. 3 shows a movable display 12 positioned over a surgical table showing an image of the patient anatomy. A target 13 may be chosen on the image of the anatomy. A remote electromagnetic transmitter, such as those commercially available from Northern Digital Incorporated (NDI) and Ascension Technology Corporation, is positioned near or under the table to localize sensors 15 on at least one medical device 16. As the display is moved, the image of the anatomy, the medical devices, projected the path 14 of the medical devices, and the collision boundaries of the medical devices is repositioned to provide the optimum view for navigation of the medical device within the anatomical image. The access points may be chosen to optimize the ability of the medical devices to reach the anatomical target without creating collisions of the medical devices that are internal and external to the patient and to optimize the ability of the medical devices to reach the target anatomy without intersecting other anatomical structures. Software may be employed to present the collision-free projected path to the anatomical target in an intuitively obvious manner by, for example, showing free path as a green line and a path with collisions as a red line.

Figure 4:
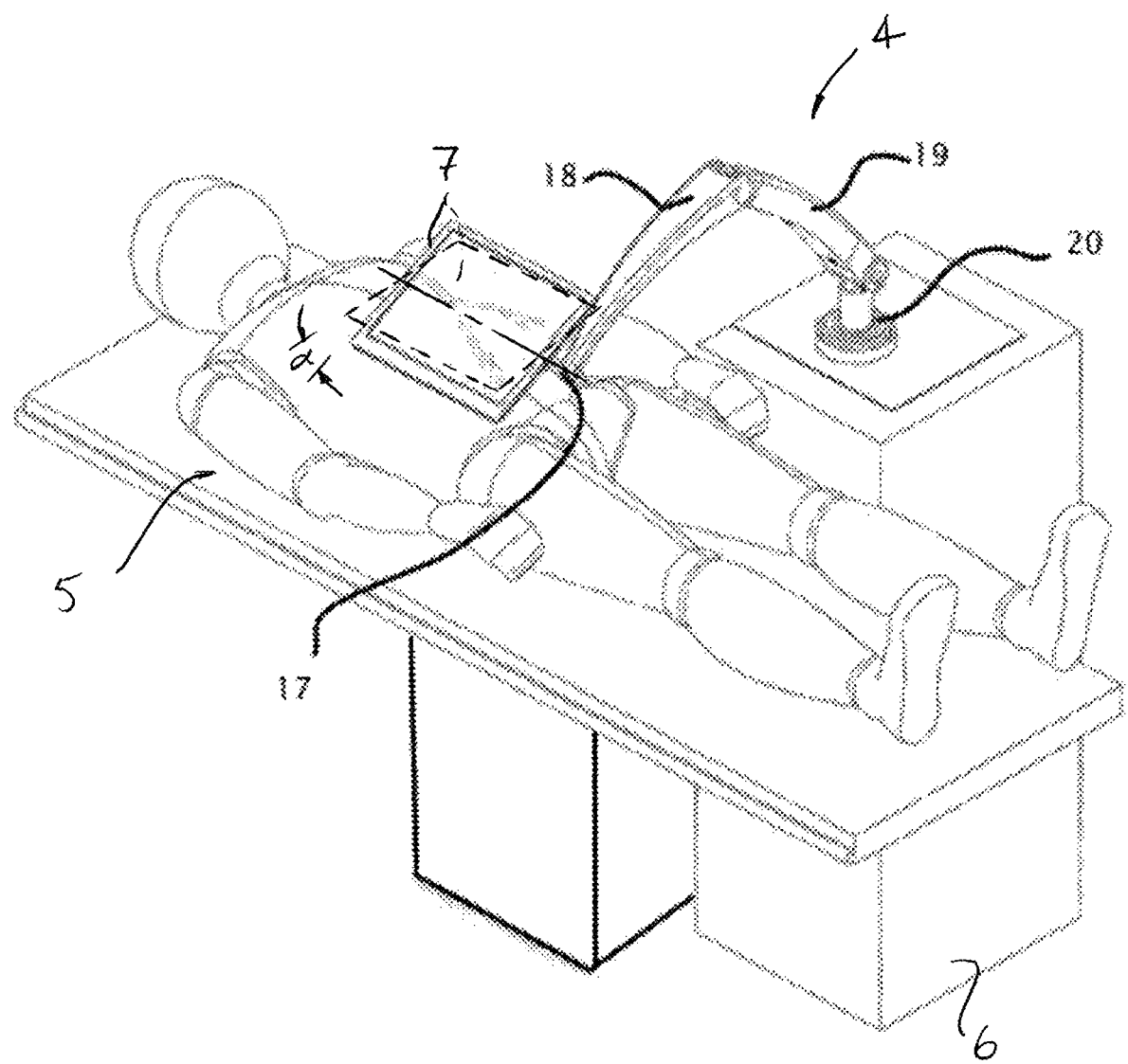
FIG. 4 is an isometric view of an embodiment of the display and support arm positioned next to the patient table.

FIG. 4 presents an embodiment of the display and support arm with counterbalanced joints at the support arm elbow 18, and shoulder 19. An additional rotational or linear joint is provided at the base of the shoulder 20 to allow the display to move along the inferior to superior axis of the patient. All support arm joints may be encoded to provide data describing the position of the display. The display support is shown in an embodiment where the arm is mounted to a portable cart that is positioned next to the patient table. Axis 17 allows the display to rotate. An alternate embodiment may attach to the table or imaging system.

Figure 5:
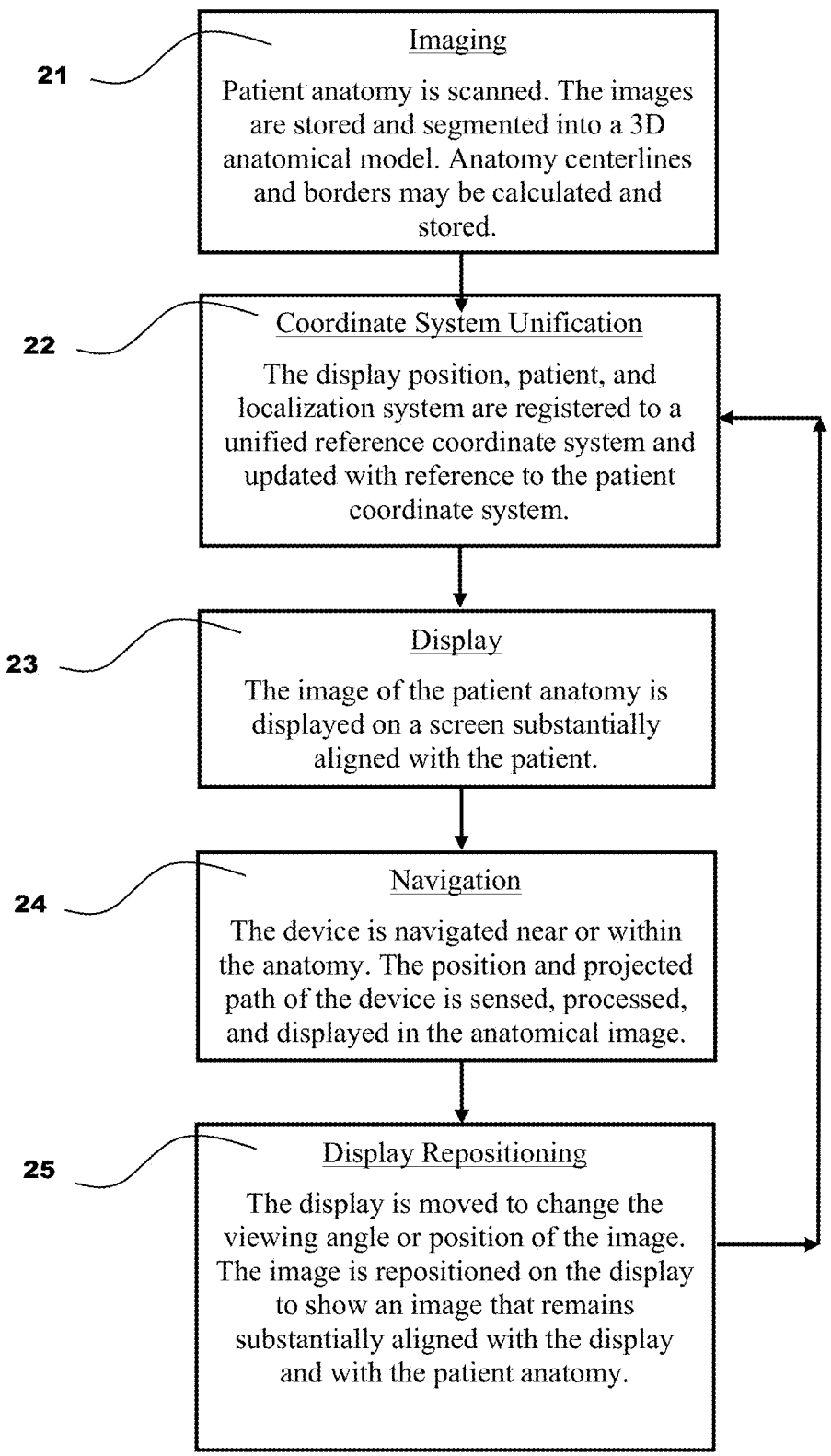
FIG. 5 is a flow chart describing the basic steps for a minimally invasive procedure using a sensored medical device and the system for displaying a co-aligned image.

FIG. 5 provides an overview of the procedure flow for a minimally invasive procedure using a stored image for navigation. The patient anatomy is scanned 21 with a non-invasive imaging modality like CT, MR, or rotational angiography. The imaged anatomy is stored and segmented into a three dimensional image, and borders and centerlines of anatomical structures are calculated using commercially available software from vendors like Philips, Siemens, GE, Toshiba, Terra Recon, Calgary Scientific, Materialise, or Osirix. The image is transferred to the memory of the system processor and the image is registered 22 to the system coordinate system along with the patient and the medical device sensors. Registration of the image may be done by imaging the patient with an image-visible skin patch, by touching a sensored probe to prominent bony an antomical points, or with an externally anatomical marker placed on the patient. At least three separate points of the patch are visible in the image and then a position sensor is placed into the patch. The visible points on the patch or bones may be selected on the displayed image and then the known distance from the marker is used to register the image to the patient position sensor. The patient position sensor and medical device position sensor are inherently registered because their positions are determined by the same sensing system. Next, the registered image is shown 23 above the patient in a manner substantially aligned to the patient anatomy. The image position may be biased slightly toward the user to provide improved ergonomics. For example, if the user is on the right side of the patient, the user may press a button on the display touch screen to inform the system of the user's operating position. The system processor will then bias the image rotationally by a small amount, usually by and angle α of 15-30 degrees (FIG. 4), toward the user. The system may also bias rotational scaling in the user's direction, creating a rotation scale factor that increases slightly as the display is moved rotationally away from the user. In this way, the image is biased toward ergonomically comfortable viewing positions for the user without losing the substantial alignment of the image to the patient that provides for improved perception and usability. The medical device may be navigated 24 within or near the patient as the position sensor in the medical device is tracked and presented as an image icon within the image of the patient anatomy. The image of the anatomy and the image of the medical device may be shown with varying degrees of transparency to maximize the visibility of the device and anatomical images. The display, showing the image of the medical device within the image of the anatomy, may be repositioned 25 to enhance the viewing angle of the anatomy. As the display is moved, the image on the screen is updated to maintain substantial alignment between the displayed anatomical image and the patient anatomy.

What is claimed is:

1. A system for displaying an image of a tool and an image of a patient's anatomy, said system comprising:
    a repositionable display screen configured to show the images of the tool and the patient's anatomy;
    a robotic device configured to control movement of the tool; and
    a processor configured to receive:
        (a) the image of the patient's anatomy;
        (b) position data and orientation data for the tool;
        (c) position data for the patient's anatomy;
        (d) position data for the display screen; and
        (e) position data for a user's position relative to the patient,
    wherein the processor is configured to:
        superimpose the image of the tool on the image of the patient's anatomy and reposition the image of the patient's anatomy on the display screen in real time based on the position data for the user's position relative to the patient so the images of both the patient's anatomy and the tool are substantially aligned with the patient as the display screen is moved over the patient,
        allow the user to selectively angle the aligned images away from the user so that when the display screen is angled toward the user, the aligned images will appear flat relative to the patient,
        receive a user input comprising a selection of an anatomical target on the image of the patient's anatomy,
        output a predicted position of the tool based on the position data for the tool and the orientation data for the tool relative to the position data for the patient's anatomy,
        project a path from the predicted position of the tool to the anatomical target,
        determine that the path is free of collisions (i) between the tool and an internal anatomy of the patient and (ii) between the tool and another medical device external to the patient,
        cause the path and an indication that the path is collision-free to be displayed on the display screen, and
        cause a collision space of the robotic device to be overlaid on the image of the patient's anatomy.

2. A system as in claim 1, wherein the processor is configured to receive a pre-operative static image of the patient's anatomy.

3. A system as in claim 1, wherein the processor is configured to receive a real time image of the patient's anatomy.

4. A system as in claim 3, wherein the real time image is fluoroscopic.

5. A system as in claim 3, wherein the real time image is a 3 dimensional point cloud of a position of the tool within the patient's anatomy.

6. A system as in claim 1, further comprising an external position tracker configured to track a position of the tool, a position of the patient's anatomy, and a position of the display screen in a reference frame.

7. A system as in claim 6, wherein:
    the external position tracker comprises a plurality of electromagnetic sensors,
    at least one of the plurality of electromagnetic sensors is present on the tool, and
    at least one of the plurality of electromagnetic sensors is affixed to the patient.

8. A system as in claim 1, further comprising an articulated support coupled to the display screen to hold the display screen over the patient, the articulated support having an encoder configured to provide the position data for the display screen to the processor.

9. A system as in claim 1, wherein the processor is configured to allow the display screen to be repositioned relative to its associated image by: interrupting a control loop within the processor between the display screen and the associated image; freezing the associated image on the display screen at the time of the interruption; and uninterrupting the control loop between the display screen and the associated image subsequent to the display screen being repositioned to a desired position.

10. A system as in claim 1, wherein the processor is configured to selectively decouple a relationship between the display screen and the image of the patient's anatomy displayed on the display screen based at least in part on a signal received from a user input device.

11. A system as in claim 1, wherein the processor is configured to change a relationship between the display screen and the image of the patient's anatomy displayed on the display screen based at least in part on a signal received from a user input device.

12. A system for displaying an image of a tool and an image of a patient's anatomy, said system comprising:
    a repositionable display screen configured to show the images of the tool and the patient's anatomy;
    a robotic device configured to control movement of the tool; and
    a processor configured to receive:
        (a) the image of the patient's anatomy;
        (b) position data for the patient's anatomy;
        (c) position data for the display screen; and
        (d) position data and orientation data for the tool;
    wherein the processor is configured to:
        superimpose the image of the tool on the image of the patient's anatomy and reposition the image of the patient's anatomy on the display screen in real time based on the position data for the display screen so the image of the both the patient's anatomy and the tool are substantially aligned with the patient as the display screen is moved, output a predicted position of the tool based on the position data for the tool and the orientation data for the tool relative to the position data for the patient's anatomy, project a path from the predicted position to an anatomical target of the patient's anatomy, determine that the path from the predicted position to the anatomical target is free of collisions (i) between the tool and another structure of the patient's anatomy and (ii) between the tool and another medical device external to the patient, output the path and an indication that the path from the predicted position to the anatomical target is free of collisions, and cause a collision space of the robotic device to be overlaid on the image of the patient's anatomy.

13. A system as in claim 12, wherein the processor is configured to track a position of the patient in real time and shift a coordinate system associated with the display screen in response to changes in position of the patient.

14. A system as in claim 12, wherein the processor is configured to receive a real time image of the patient's anatomy.

15. A system as in claim 14, wherein the real time image is ultrasonic.

16. A system as in claim 12, further comprising an external position tracker configured to track a position of the patient and a position of the display screen in a reference frame.

17. A system as in claim 16, wherein the external position tracker comprises a plurality of electromagnetic sensors.

18. A system as in claim 17, wherein:
at least one of the plurality of electromagnetic sensors is affixed to the patient, and
at least one of the plurality of electromagnetic sensors is affixed to the display screen.

19. A system as in claim 12, wherein the processor is configured to allow the display screen to be repositioned relative to its associated image by: interrupting a control loop within the processor between the display screen and the associated image; freezing the associated image on the display screen at the time of the interruption; and uninterrupting the control loop between the display screen and the associated image subsequent to the display screen being repositioned to a desired position.

20. A system as in claim 12, wherein the processor is configured to selectively decouple a relationship between the display screen and an image displayed on the display screen based at least in part on a signal received from a user input device.

21. A system as in claim 12, wherein the processor is configured to change a relationship between the display screen and an image displayed on the display screen based at least in part on a signal received from a user input device.

22. A system as in claim 12, wherein the display screen is repositionable in a first axis with a first scaling factor for the displayed image of the patient's anatomy and repositionable in a second axis different from the first axis with a second scaling factor different from the first scaling factor for the displayed images, the first axis comprising a first translational axis or a first rotational axis, and the second axis comprising a second translational axis different from the first translational axis or a second rotational axis different from the first rotational axis.

23. A system as in claim 22, wherein the first scaling factor is in a range between 1:1 and 1.5:1.

24. A system as in claim 22, wherein the second scaling factor is in a range between 1:1 and 1.5:1.

25. A system as in claim 1, wherein the processor is configured to freeze the aligned images on the display screen while the display screen is being repositioned, unfreeze the aligned images after the display screen has been repositioned, and resume the alignment of the images with the patient as the display screen is further moved over the patient.

26. A system as in claim 12, wherein the processor is configured to freeze images on the display screen while the display screen is being repositioned, and unfreeze images on the display screen after the display screen has been repositioned.

27. A system as in claim 1, wherein the processor is configured to cause another path from the predicted position to the selected anatomical target that includes at least one collision to be displayed.

28. A system as in claim 12, wherein the processor is configured to:
cause another path from the predicted position to the anatomical target to be displayed on the display screen along with another indication that the another path is not free of collisions.

29. A system as in claim 1, wherein the indication is a first indication displayed on the display screen in response to determining that the path from the predicted position to the anatomical target is collision-free, wherein the processor is further configured to display on the display screen a second indication in response to determining that the path from the predicted position to the anatomical target is not collision-free.

30. A system as in claim 12, wherein the indication is a first indication outputted in response to determining that the path from the predicted position to the anatomical target is collision-free, wherein the processor is further configured to output a second indication in response to determining that the path from the predicted position to the anatomical target is not collision-free.

31. A system, comprising:
a display comprising a display position sensor configured to generate position data;
a medical tool configured to be inserted into a patient's anatomy, the medical tool comprising a sensor configured to generate position data and orientation data for the medical tool;
a patient reference sensor configured to generate position data for the patient's anatomy;
a robotic device configured to control movement of the medical tool; and
a processor configured to:
generate an image on the display comprising a position of the medical tool with respect to the patient's anatomy superimposed on an image of the patient's anatomy based on the position data for the medical tool and the position data for the patient's anatomy,
determine that a path from the position of the medical tool to an anatomical target is free of collisions (i) between the medical tool and an internal anatomy of the patient and (ii) between the medical tool and another medical device external to the patient, based on the orientation data of the medical tool,
cause the path to be displayed on the display,
output an indication that the path is collision-free, and
cause a collision space of the robotic device to be overlaid on the image of the patient's anatomy.

32. A system as in claim 31, wherein the processor is further configured to:
  apply a rotational bias to the image on the display toward a user based on the position data for the display and position data for a user's position relative to the patient's anatomy, and
  adjust an amount of the rotational bias applied to the image in response to the display being moved rotationally with respect to the user.

33. A system as in claim 31, wherein the image of the patient's anatomy is a pre-operative image, and wherein the image on the display further comprises an intra-operative endoscopic image of the patient's anatomy superimposed on the pre-operative image.

34. A system as in claim 31, wherein the processor is further configured to:
  detect movement of the display based on the position data for the display, and
  cause re-positioning of the medical tool in response to the detected movement of the display.

35. A system as in claim 31, wherein the processor is further configured to:
  indicate that the path is collision-free by causing the path to be displayed as a green line on the display, and
  indicate that a second path involves a collision by causing the second path to be displayed as a red line on the display.

* * * * *